US012573031B2

(12) United States Patent
Sousa Ferreira et al.

(10) Patent No.: US 12,573,031 B2
(45) Date of Patent: Mar. 10, 2026

(54) AUTOMATIC DETECTION OF EROSIONS AND ULCERS IN CROHN'S CAPSULE ENDOSCOPY

(71) Applicant: DIGESTAID—ARTIFICIAL INTELLIGENCE DEVELOPMENT, LDA, Gondomar (PT)

(72) Inventors: João Pedro Sousa Ferreira, Oporto (PT); Miguel José Da Quinta E Costa De Mascarenhas Saraiva, Oporto (PT); Hélder Manuel Casal Cardoso, Valbom Gondomar (PT); Manuel Guilherme Goncalves De Macedo, Oporto (PT); João Pedro Lima Afonso, Mazedo Moncao (PT); Ana Patricia Ribeiro Andrade, Oporto (PT); Renato Manue Natal Jorge, Oporto (PT); Marco Paulo Lages Parente, Oporto (PT)

(73) Assignee: Digestaid—Artificial Intelligence Development, LDA, Gondomar (PT)

( * ) Notice: Subject to any disclaimer, the term of this patent is extended or adjusted under 35 U.S.C. 154(b) by 265 days.

(21) Appl. No.: 18/037,992

(22) PCT Filed: Nov. 19, 2021

(86) PCT No.: PCT/PT2021/050041
§ 371 (c)(1),
(2) Date: May 19, 2023

(87) PCT Pub. No.: WO2022/108466
PCT Pub. Date: May 27, 2022

(65) Prior Publication Data
US 2024/0020829 A1     Jan. 18, 2024

(30) Foreign Application Priority Data

Nov. 19, 2020    (PT) ........................................ 116896

(51) Int. Cl.
*G06T 7/00* (2017.01)
*A61B 1/04* (2006.01)

(52) U.S. Cl.
CPC ............ *G06T 7/0012* (2013.01); *A61B 1/041* (2013.01); *G06T 2207/10068* (2013.01);
(Continued)

(58) Field of Classification Search
None
See application file for complete search history.

(56) References Cited

U.S. PATENT DOCUMENTS

2011/0245611 A1* 10/2011 Yeh ........................ A61B 1/041
                                                                    600/118
2019/0148021 A1* 5/2019 Styner .................... G06N 20/10
                                                                    705/2
(Continued)

FOREIGN PATENT DOCUMENTS

EP        3 659 143      * 9/2019

OTHER PUBLICATIONS

Li, Baopu, and Max Q-H. Meng. "Automatic polyp detection for wireless capsule endoscopy images." Expert Systems with Applications 39.12 (2012): 10952-10958. (Year: 2012).*
(Continued)

*Primary Examiner* — Andrae S Allison
(74) *Attorney, Agent, or Firm* — Heisler & Associates

(57) ABSTRACT

The present invention relates to a computer-implemented method capable of automatically detecting small bowel and colonic ulcers and erosions in Crohn's capsule endoscopy image data, by classifying pixels as lesion or non-lesion, using a convolutional image feature extraction step followed by a classification step and indexing such lesions in the set of one or more classes.

11 Claims, 12 Drawing Sheets

(52) U.S. Cl.
CPC .............. *G06T 2207/20081* (2013.01); *G06T 2207/20084* (2013.01); *G06T 2207/30028* (2013.01); *G06T 2207/30096* (2013.01)

(56) References Cited

U.S. PATENT DOCUMENTS

2019/0180153 A1* 6/2019 Buckler .................. G06F 18/29
2021/0076960 A1* 3/2021 Fornwalt ................ A61B 5/282

OTHER PUBLICATIONS

Sun, Muyi, et al. "Non-local attention and densely-connected convolutional neural networks for malignancy suspiciousness classification of gastric ulcer." IEEE Access 8 (2020): 15812-15822. (Year: 2020).*

Liu, Hao, et al. "Hybrid model structure for diabetic retinopathy classification." Journal of Healthcare Engineering 2020.1 (2020): 8840174. (Year: 2020).*

Pavel, Zahradn 'kova' A, jr. (2019) Automatic assessment of the cardiomyocyte development stages from confocal microscopy images using deep convolutional networks. PLoS (Year: 2019).*

Aoki, Tomonori, et al. "Automatic detection of erosions and ulcerations in wireless capsule endoscopy images based on a deep convolutional neural network." Gastrointestinal endoscopy 89.2 (2019): 357-363. (Year: 2019).*

Patent Cooperation Treaty, Written Opinion and International Search Report issued in PCT/PT2021/050041, Mar. 14, 2022, pp. 1-16.

Valerio et al., "Lesions Multiclass Classification in Endoscopic Capsule Frames", Procedia Computer Science, 2019, pp. 637-645, vol. 164.

Wang et al., "A systematic evaluation and optimization of automatic detection of ulcers in wireless capsule endoscopy on a large dataset using deep convolutional neural networks", Physics in Medicine and Biology, Institute of Physics Publishing, Dec. 5, 2019, pp. 1-13, vol. 64(23).

Yan et al., "Intelligent diagnosis of gastric intestinal metaplasia based on convolutional neural network and limited humber of endoscopic images", Computers in Biology and Medicine, Oct. 12, 2020, pp. 1-8, vol. 126.

Kyriakides et al., "An Introduction to Neural Architecture Search for Convolutional Networks", arxiv.org, University of Macedonia, May 22, 2020, pp. 1-17.

* cited by examiner

FIG. 7

| Evaluation of method 9000 | Best overall accuracy (mean ± standard deviation in %) | |
|---|---|---|
| | with method 8000 (our method) | without method 8000 |
| VGG | 97.2 ± 1.0 | 93,4 |
| ResNet50 | 98.3 ± 1.2 | 97,1 |
| ResNet125 | 98.7 ± 1.2 | 96,4 |
| InceptionV3 | 98.8 ± 0.7 | 97,8 |
| MobileNet | 95.5 ± 0.8 | 92,4 |
| Xception | 98.9 ± 0.5 | 97,9 |
| EfficientNetB3 | 96.7 ± 1.7 | 95,7 |
| EfficientNetB5 | 98.4 ± 0.9 | 97,3 |
| EfficientNetB7 | 99.1 ± 0.5 | 98,4 |

AUTOMATIC DETECTION OF EROSIONS AND ULCERS IN CROHN'S CAPSULE ENDOSCOPY

RELATED PATENT APPLICATIONS

This patent application is the National Phase of International Application No. PCT/PT2021/050041, filed Nov. 19, 2021, which designated the U.S. and that International Application was published under PCT Article 21(2) in English, which claims the benefit of priority to Portuguese Patent Application No. 116896, filed Nov. 19, 2020. The entire contents of the foregoing applications are incorporated herein by reference, including all text, tables and drawings.

BACKGROUND OF THE INVENTION

The present invention relates to lesion detection and classification in medical image data. More particularly, to automated identification of small bowel and colonic ulcers and erosions in Crohn's capsule endoscopy images, therefore assessing the inflammatory bowel activity.

Crohn's capsule endoscopy is an invaluable non-invasive tool for the detection of erosions ad ulcers. By carefully examining the video frames of the Crohn's capsule, physicians can detect, identify and characterize ulcers and erosions lesions in the mucosa of the gastrointestinal tract. However, such examination of Crohn's capsule endoscopy images is significantly time-consuming for gastroenterologists and prone to human error and oversight. Conversely, in Crohn's capsule endoscopy, the record of such images is readily available and can be digitally stored for posterior review and comparison. Within this context, image data creates a robust and fertile ground for computer-aided diagnosis using machine learning systems for lesion characterization and, consequently, decision making. The goal of the erosions and ulcers detection of the small bowel and colonic lesions is to yield a more accurate, thoroughly automated characterization of the mucosal injury and subsequently measure the bowel inflammatory activity, aiding in the medical diagnosis and treatment.

Valério, Maria Teresa, et al. In "Lesions Multiclass Classification in Endoscopic Capsule Frames." Procedia Computer Science 164 (2019): 637-645 raised awareness for the time-consuming and error-prone identification of small bowel lesions by medical experts. Furthermore, the authors proposed an automatic approach for identifying these lesions based on deep learning networks on medically annotated wireless capsule endoscopy images.

Document CN111127412A provides a pathological image recognition device based on a generation countermeasure network, aiming at solving the problems of dependence on experience, high manual labeling cost, low recognition efficiency, and poor accuracy of the existing pathological recognition method. The method is evaluated for Crohn's disease lesions but does not distinguish which type of lesion each image presents.

Document CN107730489A discloses wireless capsule endoscope small intestine lesion meter of efficiently and accurately calculation machine assisted detection system and detection method, using deep learning thought as technological core, utilize the convolution in deep learning model neutral net (Convolutional Neural Network, CNN) algorithm builds different graders, realizes capsule endoscope. The classification and positioning of small intestine lesion and the extraction to focus and to obtain lesion position is realized using image segmentation algorithm. However, it does not use transfer learning and does not update training data with the new data for the next training generation.

Document CN111340094A, although it discloses a capsule endoscope image auxiliary classification method based on deep learning, does not use transfer learning. It does not update training data with the new data for the next training generation, such as disadvantages such as requirements for extensive datasets of endoscopic images. Also, with such methods, only a minimal number of categories can be used.

Document CN111739007A shows a bubble area identifier trained by a convolutional neural network. Although it uses similar a learning method, it does not classify ulcers or erosions lesions.

Document WO 2020079696 A1 discloses a system to generate and display images of the gastrointestinal tract from capsule endoscopy. The invention does not apply any specific method of artificial intelligence for image classification. The invention provides a platform to deploy methods applied on images. It does not apply convolutional neural networks for image classification.

Document US 2020286219 A1 presents a method for detection similar images and image classification from video capsule endoscopy. The invention does not apply optimized training sessions for image classification. The method of the invention does not distinguish blood and other colon lesions from capsule endoscope images.

Document US 2018296281 A1 shows a control system for capsule endoscopes based on machine learning image feature recognition. The system controls capsule orientation by calculating the center of mass of the detected image feature. The invention does not apply methods for image classification in capsule endoscope images.

Gastrointestinal diseases, such as internal lesions in the small bowel, are currently one of the most common diseases and very often, when not removed, these may evolve into cancer. Colonoscopy is a time-consuming and repetitive task and occasionally the endoscopist may present signs of fatigue or suffer from an attention deficit, failing to accurately identify all the manifestations of such diseases. Endoscopic image acquisitions are the state-of-the-art technique for an insight into the patients' intestinal tract. Usually, the endoscopic elements are provided with a portable image recording device and means to convert these captures to a digitized representation and capable of being stored in a personal computer.

Endoscopic images, due to the nature of their acquisition, often lack the light or other photographic conditions to allow the classification of small bowel/colon straightforwardly executed. Within this context, machine learning techniques have been presented to automatically execute such task but up-to-date they have failed to present overall accuracy or false-negative rate that can be used in clinical practice and hence leads to inappropriate treatment

BRIEF SUMMARY OF THE INVENTION

The present invention provides a method for deep learning based identification of erosions and ulcers of the small bowel and colon in endoscopic images and indirectly measuring inflammatory bowel activity. Indeed, the gold standard for assessing bowel inflammatory activity is the direct visualization of the bowel mucosa. The automatic identification of erosions/ulcers is vital to determine small bowel and colon inflammatory status lesions, crucial for diagnosis and treatment planning.

By using trained convolutional layers of different architecture on the ImageNet[1] dataset and further testing them using sample of the CCE image stack, the potential to detect injuries is shown. The disruptive clinical nature of the present invention is justified by the artificial intelligence system's ability to detect pleomorphic mucosal injuries, particularly erosions and ulcers, therefore measuring inflammatory bowel activity. Indeed, this novel neural network AI based approach, capable to automatically identify lesions of subtle pleomorphic nature, is of the utmost importance in clinical practice, allowing a complete Crohn's capsule endoscopy diagnosis. Furthermore, the specific application of a tailor-made artificial intelligence system to Crohn's capsule endoscopy is a relevant novelty introduced by this invention to the current state of the art. One of the most critical and frequent indications for performing Crohn's capsule endoscopy is inflammatory bowel disease. Correct assessment of erosions and ulcers in the endoscopic findings is vital for clinical follow-up management. Therefore, by accurately identifying ulcers and erosions in Crohn's capsule endoscopy, the present invention helps the clinical team better define the diagnostic and therapeutic management of the patient, which may translate into optimized clinical outcomes.

The following were considered relevant to highlight the problem solved by the present invention from the methods known in the art to detect and classify small bowel/colon ulcers and erosions in Crohn's capsule endoscopy.

In one embodiment of the method detects relevant ulcers and erosions in Crohn's capsule endoscopy images. Ulcers and erosions identification in Crohn's capsule endoscopy is vital to assess inflammatory bowel activity. Furthermore the invention uses transfer learning and semi-active learning. Transfer learning allows feature extraction and high-accuracy classification using reasonable datasets sizes. The semi-active implementation allows a continuous improvement in the classification system. Furthermore, the invention preferably uses transfer learning for feature extraction on Crohn's capsule endoscopy images or semi-active learning strategy for Crohn's capsule endoscopy images.

Another embodiment of the method splits the dataset into a number of stratified folds, where images relative to a given patient are included in one fold only. Further, additionally or alternatively, such data is trained and validated with patient grouping to a random fold, i.e., images from an arbitrary patient belong to either the training or the validation set.

Preferred is a method which uses the chosen training and validation sets to further train a series of network architectures, which include, among others, a feature extraction, and a classification component. The series of convolutional neural networks to train include but are not limited to: VGG16, InceptionV3, Xception EfficientNetB5, EfficientNetB7, Resnet50, and Resnet125. Preferably, their weights are frozen, with exception to the BatchNormalization layers, and are coupled with a classification component. The classification component comprises at least two dense layers, preferably of sizes 2048 and 1024, and at least one dropout layer of preferably 0.1 in between them.

Alternatively, but not preferentially, the classification component can be used with more dense layers or with dense layers of different size. Alternatively, but not preferentially, the classification component can also be used without dropout layers.

Further, additionally, and preferably, the best performing architecture is chosen according to the overall accuracy and sensitivity. Performance metrics include but are not limited to f1-metrics. Further, the method is not limited to two to four dense layers in sequence, starting with 4096 and decreasing in half up to 512. Between the final two layers there is a dropout layer of 0.1 drop rate.

Lastly, the best performing solution is trained using the complete dataset with patient grouping.

Further embodiments of the present invention may include similar classification networks, training weights and hyperparameters.

These may include the usage of any image classification network, new or not yet designed.

In general, the method includes two modules: prediction and output collector. Prediction reads videos and flags images with findings. Conversely, the output collector passes these images with findings for processing.

Examples of advantageous effects of the present invention include: training using parameters from machine learning results of cloud-based every-day increasing datasets; automatically prediction of the endoscopy image by using a deep learning method so that the small bowel and colon lesions from image input of the Crohn's capsule endoscope can be identified and classified into normal mucosa or ulcers/erosions; the usage of transfer learning improves the image classification speed and corresponding classification accuracy.

BRIEF DESCRIPTION OF THE DRAWINGS

FIG. 7 illustrates exemplary accuracy curves during training on a small subset of images and labelled data and according to an embodiment of the present invention. Example of results from an iteration of method 8000.

FIG. 11 illustrates a result of performing deep learning-based lesion classification on the data volume 240 and 250, according to an embodiment of the present invention.

DETAILED DESCRIPTION

The present invention discloses a new method and system capable of detecting and classifying small bowel and colonic ulcers and erosions in images acquired during a Crohn's capsule endoscopy exam.

Some preferable embodiments will be described in more detail with reference to the accompanying drawings, in which the embodiments of the present disclosure have been illustrated. However, the present disclosure can be implemented in various manners, and thus should not be construed to be limited to the embodiments disclosed herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

The term "deep learning" is a machine learning technique that uses multiple data processing layers to classify the data sets with high accuracy. It can be a training network (model or device) that learns based on a plurality of inputs and outputs. A deep learning network can be a deployed network (model or device) generated from the training network and provides an output response to an input.

The term "supervised learning" is a deep learning training method in which the machine is provided with already classified data from human sources. In supervised learning, features are learned via labeled input.

The term "convolutional neural networks" or "CNNs" are networks that interconnect data used in deep learning to recognize objects and regions in datasets. CNNs evaluate raw data in a series of stages to assess learned features.

The term "transfer learning" is a machine storing the information learned when attempting to solve one problem to solve another problem of similar nature as the first.

The term "semi-active learning" is used as a process of machine learning. Before executing the next learning process, the training network appends a set of labeled data to the training dataset from a trusted external entity. For example, as a machine collects more samples from specialized staff steps, the less prone it is to mispredict images of identical characteristics.

The term "computer-aided diagnosis" refers to machines that analyze medical images to suggest a possible diagnosis.

The term "ulcers and erosions" represent mucosal breaks in the mucosa of the small bowel or the colon. These lesions are distinguished based on estimated size and depth of penetration. "Ulcers" were defined as a depressed loss of epithelial covering, with a whitish base and surrounding swollen mucosa with >5 mm of diameter. Conversely, mucosal erosions were defined as a minimal loss of epithelial layering surrounded by normal mucosa.

Figure 1:
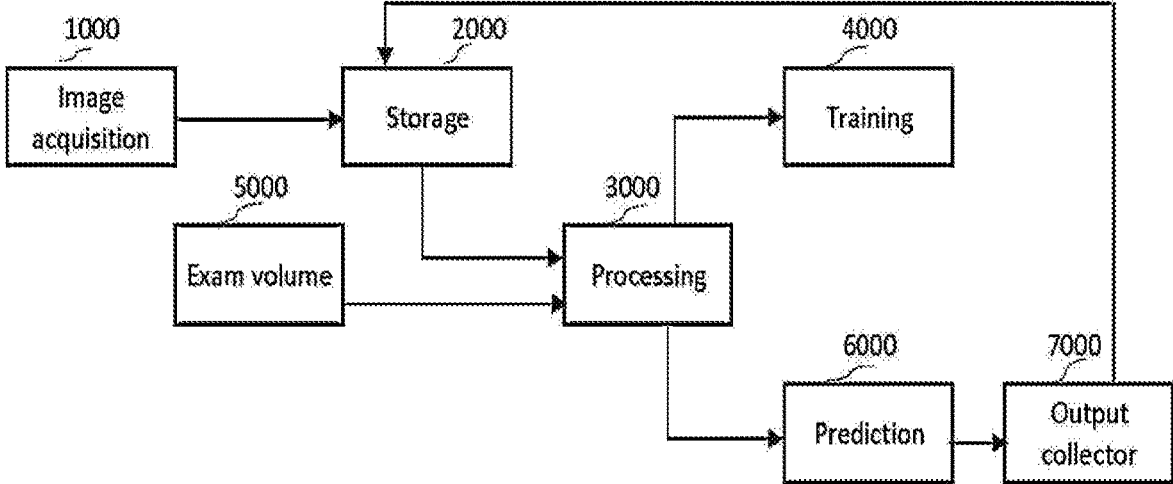
FIG. 1 illustrates a method for detection of erosions and ulcers in Crohn's Capsule Endoscopy according to an embodiment of the present invention.

The present invention relates to a method for deep learning based method for detection of erosions and ulcers in Crohn's capsule endoscopic images (FIG. 1). Often, embodiments of the present invention provide a visual understanding of the deep learning erosion and ulcer detection method. Automatic lesion classification of small bowel and colon images in Crohn's capsule endoscopy is a challenging task since lesions with different bleeding potential have similar shape and contrast. Large variations in the gastrointestinal tract preparation before Crohn's capsule ingestion further complicates automated small bowel and colon lesion classification.

Although the automatic training and classification times is fast (on average 10 seconds for a test dataset of 2000 images), the output is not satisfactory for a fast diagnosis by the experts.

A method is described for small bowel and colon lesion classification in Crohn's capsule endoscopy according to an embodiment of the present invention. The method comprises an image acquisition module, a storage module, a training input module, a processing module, an exam input module, a training module, a prediction module, and an output collector module.

Figure 4:
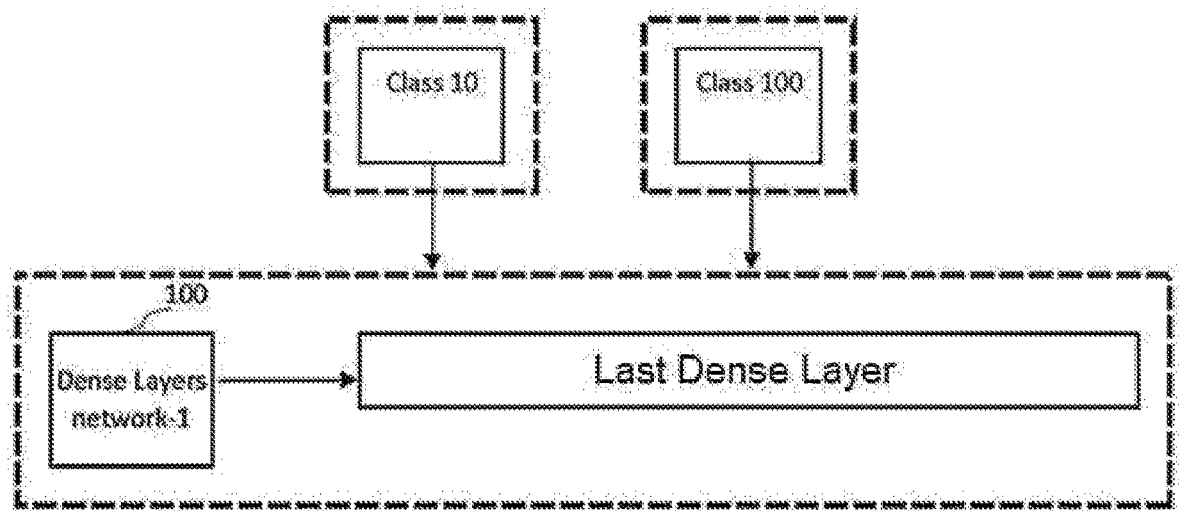
FIG. 4 illustrates the structure of the classification network to distinguish according to bleeding potential.

The image acquisition module 1000 receives exam input volumes from Crohn's capsule endoscopy providers. Images and corresponding labels are loaded onto the storage module 2000. The storage module 2000 includes a multitude of classification network architectures 100, trained convolutional network architectures 110 and hyperparameters for training. The storage module 2000 can be a local or cloud server. The storage module contains training input labelled data from Crohn's capsule endoscopy images and the required metadata to run processing module 3000, training module 4000, prediction module 5000, a second prediction module 6000, and output collector module 7000. The input labelled data includes, but not only, images and corresponding lesion classification. The metadata includes, but not only, a multitude of classification networks architectures 100 exemplified in FIG. 4, a multitude of trained convolutional neural networks architectures 110, training hyperparameters, training metrics, fully trained models, and selected fully trained models.

Images 1000 and labelled data are processed at the processing module 3000 before running the optimized training at the training module 4000. The processing module normalizes the images according to the deep model architecture, to be trained at 3000 or evaluated at 4000. By manual or scheduled request, the processing module normalizes the image data at the storage module 2000 according to the deep model architectures that will run at training module 4000. Additionally, the processing module generates the data pointers to the storage module 2000 to form the partial or full images and ground-truth labels required to run the training module 3000. To prepare each training session, a dataset is divided folds, where patient-specific imagery is exclusive to one and one fold only, for training and testing. The training set is split for model training to generate the data pointers of the all images and ground-truth labels, required to run the training process 9000. K-fold is applied with stratified grouping by patient in the training set to generate the data pointers of the partial images and ground-truth labels, required to run the model verification process 8000 of the training module 4000. The split ratios and number of folds are available at the metadata of the storage module. Operators include but are not limited to users, a convolutional neural network trained to optimize the k-fold or a mere computational routine. Merely as an example, the dataset is divided with patient split into 90% for training and 10% for testing. Optionally, images selected for training can be split into 80% for training and 20% for validation during training. A 5-fold with stratified grouping by patient is applied in the images selected for training. By manual or scheduled request, the processing module normalizes the exam volume data 5000 according to the deep model architecture to run at the prediction module 6000.

7

Figure 2:
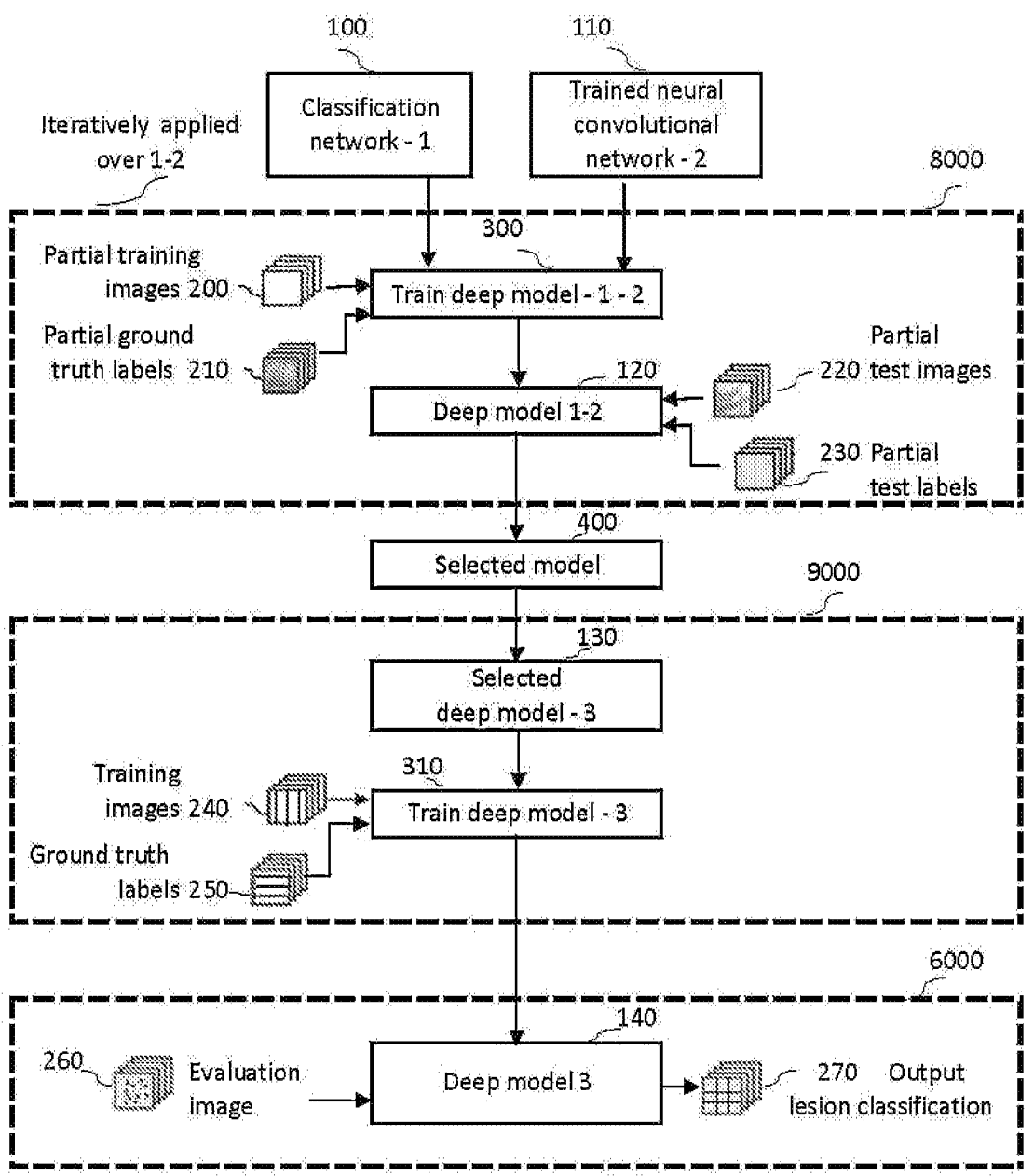
FIG. 2 illustrates the method for automatic detection and differentiation of erosions and ulcers in Crohn's Capsule Endoscopy exam.
Figure 3:
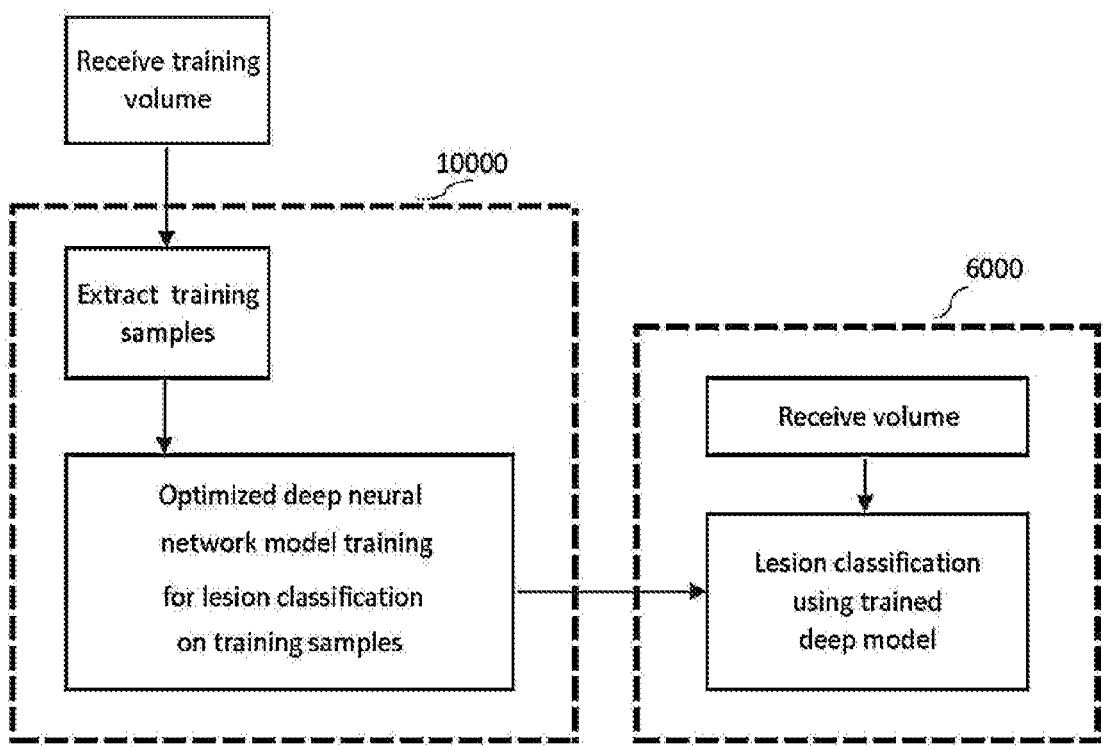
FIG. 3 illustrates the major processes for automatic detection and differentiation of erosions and ulcers in Crohn's Capsule Endoscopy exam.

As seen in FIG. 2, the training module 4000 has a model verification process 8000, a model selection step 400 and a model training step 9000. The model verification part iteratively selects combinations of classification architectures 100 and convolutional networks 110 to train a deep model for small bowel and colon lesion classification. The classification network 100 has Dense and Dropout layers to classify small bowel and colon lesions according to their hemorrhagic potential. A neural convolutional network 110 trained on large datasets is coupled to the said classification network 100 to train a deep model 300. Partial training images 200 and ground-truth labels 210 train the said deep model 300. The performance metrics of the trained deep model 120 are calculated using a plurality of partial training images 220 and ground-truth labels 230. The model selection step 400 is based on the calculated performance metrics, such as f–1. The model training part 9000 trains the selected deep model architecture 130, at process 310, using the entire data of training images 240 and ground-truth labels 250. At the prediction module 6000, the trained deep model 140 outputs small bowel and colon lesion classification 270 from a given evaluation image 260. An exam volume of data 5000 comprising the images from the Crohn's capsule endoscopy video is the input of the prediction module 6000. The prediction module 6000 classifies image volumes of the exam volume 5000 using the best-performed trained deep model from 4000 (see FIG. 3). An output collector module 7000 receives the classified volumes and load them to the storage module after validation by another neural network or any other computational system adapted to perform the validation task.

Merely as exemplificative, the invention comprises a server containing training results for architectures in which training results from large cloud-based large datasets such as, but not only, ImageNet, ILSVRC, and JFT. The architecture variants include, but are not limited to, VGG, ResNet, Inception, Xception or Mobile, EfficientNets. All data and metadata can be stored in a cloud-based solution or on a local computer. Embodiments of the present invention also provide various approaches to make a faster deep model selection. FIG. 2 illustrates a method for deep learning small bowel and colon lesion classification according to an embodiment of the present invention. The method of FIG. 2 includes a pretraining stage 8000, a training stage 9000. The training stage 8000 is performed with early stopping on small subsets of data to select the best-performed deep neural network for small bowel and colon lesion classification among multiple combinations of convolution and classification parts. For example, a classification network of two dense layers of size 512 is coupled with the Xception model to train on a random set resulting from k-fold cross validation with patient grouping. Another random set is selected as the test set.

The process of training 8000 with early stopping and testing on random subsets is repeated in an optimization loop for combinations of (i) classification and transfer-learned deep neural networks; (ii) training hyperparameters. The image feature extraction component of the deep neural network is any architecture variant without the top layers accessible from the storage module. The layers of the feature extraction component remain frozen but are accessible at the time of training via the mentioned storage module. The BatchNormalization layers of the feature extraction component are unfrozen, so the system efficiently trains with Crohn's capsule endoscope images presenting distinct features from the cloud images. The classification component has at least two blocks, each having, among others, a Dense layer followed by a Dropout layer. The final block of the classification component has a BatchNormalization layer followed by a Dense layer with the depth size equal to the number of lesions type one wants to classify.

The fitness of the optimization procedure is computed to (i) guarantee a minimum accuracy and sensitivity at all classes, defined by a threshold; (ii) minimize differences between training, validation, and test losses; (iii) maximize learning on the last convolutional layer. For example, if a training shows evidence of overfitting, a combination of a shallow model is selected for evaluation.

The training stage 9000 is applied on the best performed deep neural network using the whole dataset.

The fully trained deep model 140 can be deployed onto the prediction module 6000. Each evaluation image 260 is then classified to output a lesion classification 270. The output collector module has means of communication to other systems to perform expert validation and confirmation on newly predict data volumes reaching 270. Such means of communication include a display module for user input, a thoroughly trained neural network for decision making or any computational programmable process to execute such task. Validated classifications are loaded on the storage module to become part of the datasets needed to run the pipelines 8000 and 9000, either by manual or schedule requests.

Figure 5:
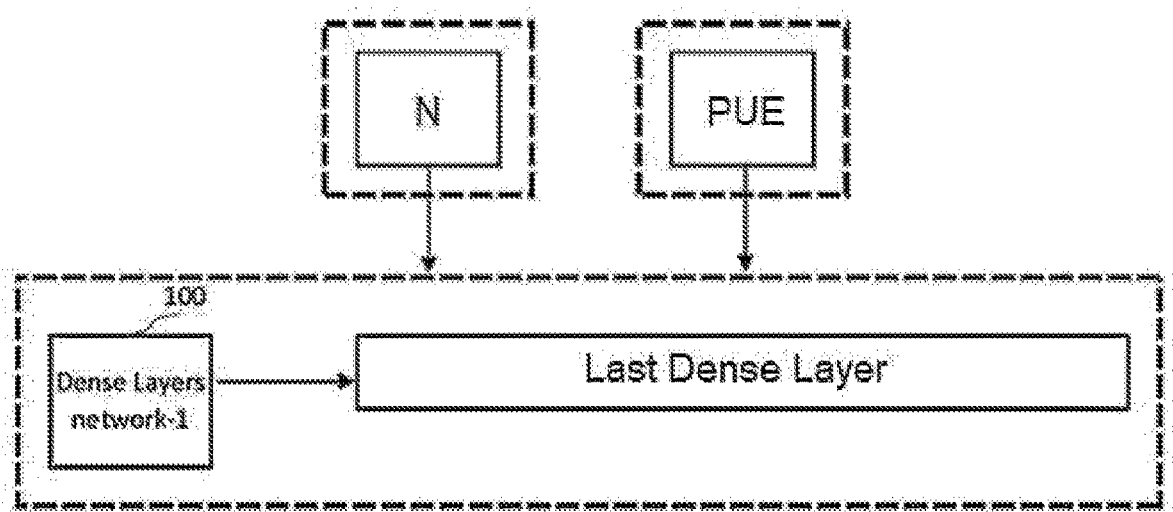
FIG. 5 depicts an embodiment of the classification network to classify according to bleeding potential.
Figure 6:
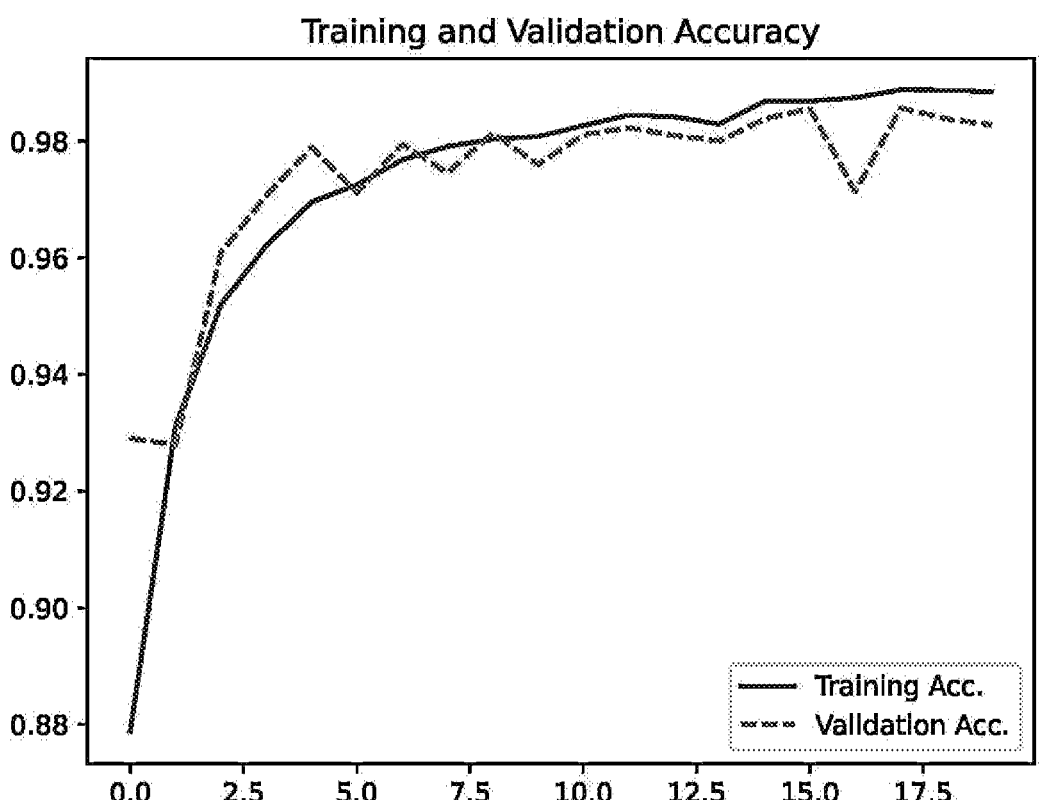
FIG. 6 illustrates a preferable embodiment of the present invention where the accuracy curves for the training on a small subset of images and labelled data are shown. Example of results from an iteration of method 8000.
Figure 7:
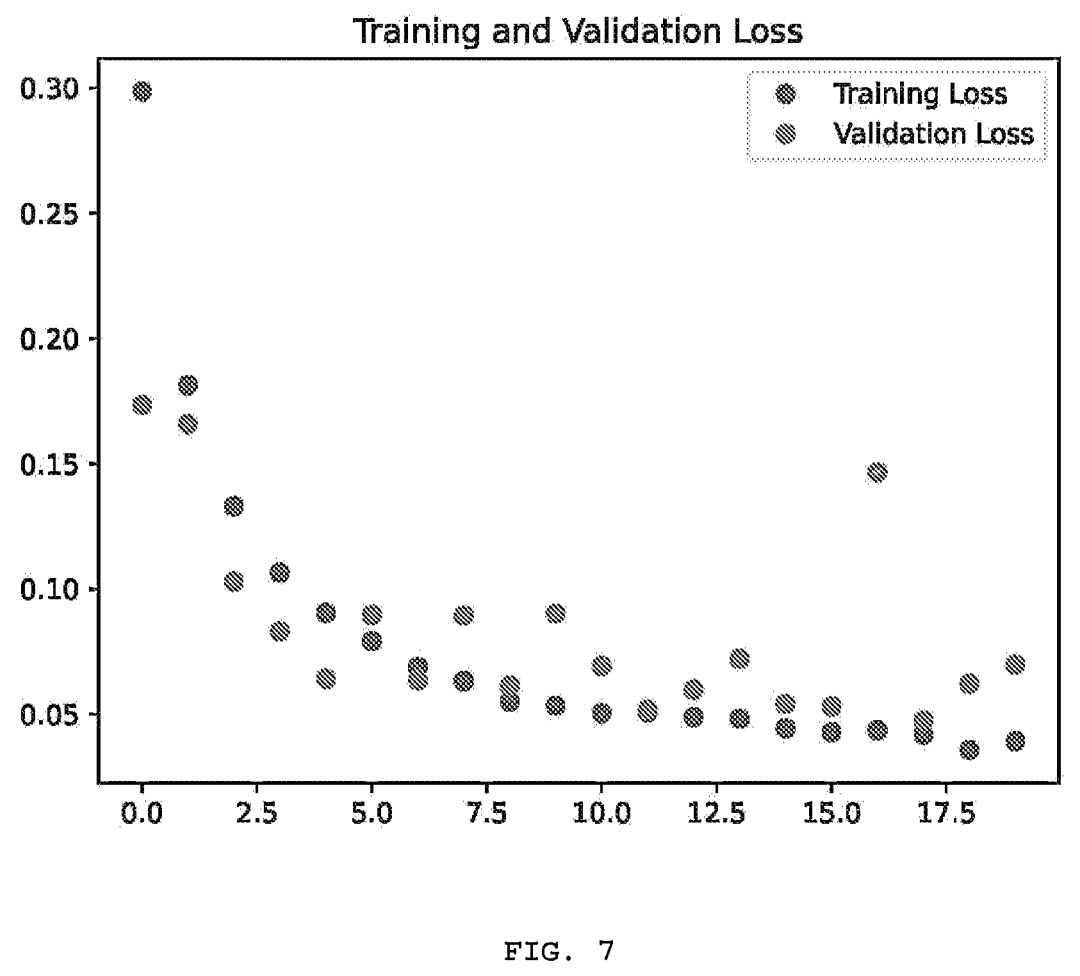

An embodiment of the classification network 100, as seen in FIG. 5, can classify according to bleeding potential as N: normal; PUE: ulcers or erosion; are shown and grouped accordingly. At a given iteration of method 8000 (FIGS. 7, 8, and 9), the optimization pipeline described herein uses accuracy curves, ROC curves and AUC values and confusion matrix from training on a small subset of images and labelled data.

Figure 8:
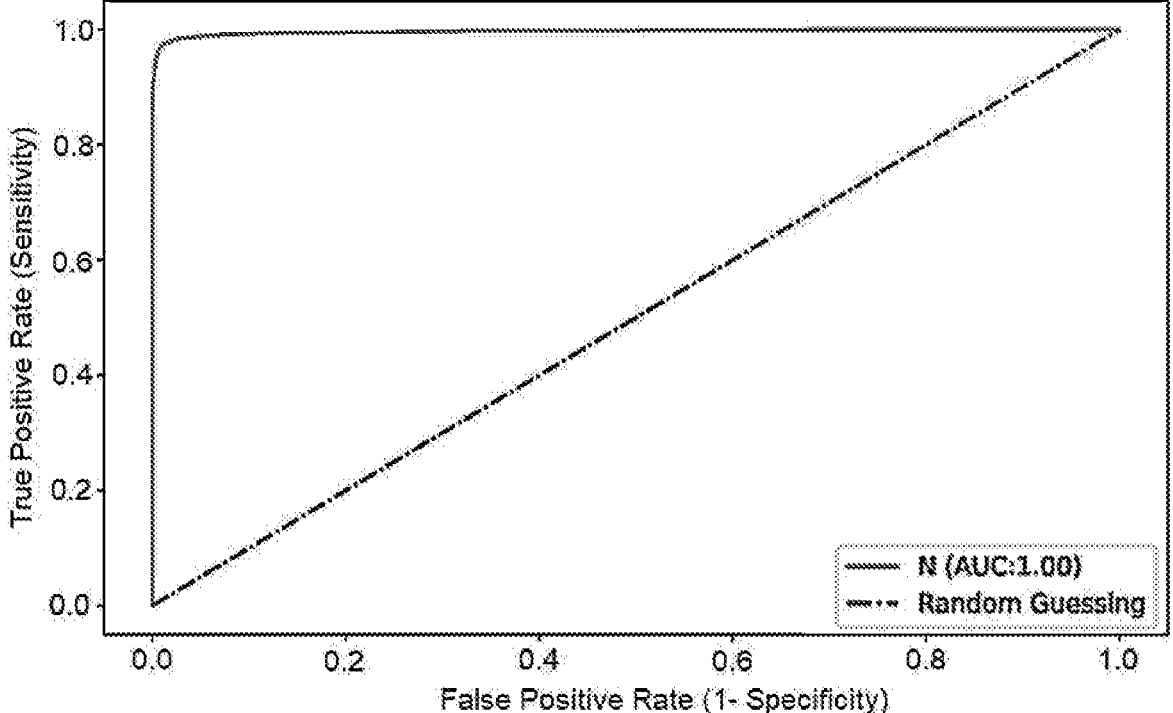
FIG. 8 illustrates exemplary ROC curves and AUC values obtained after training on a small subset of images and labelled data according to an embodiment of the present invention. Results used for model selection. Example of results from an iteration of method 8000, and a zoom of the ROC curves.

FIG. 8 illustrates exemplary ROC curves and AUC values obtained after training on a small subset of images and labelled data where 10 (N-AUC: 1.00) and 12 represent the Random Guessing.

Figure 9:
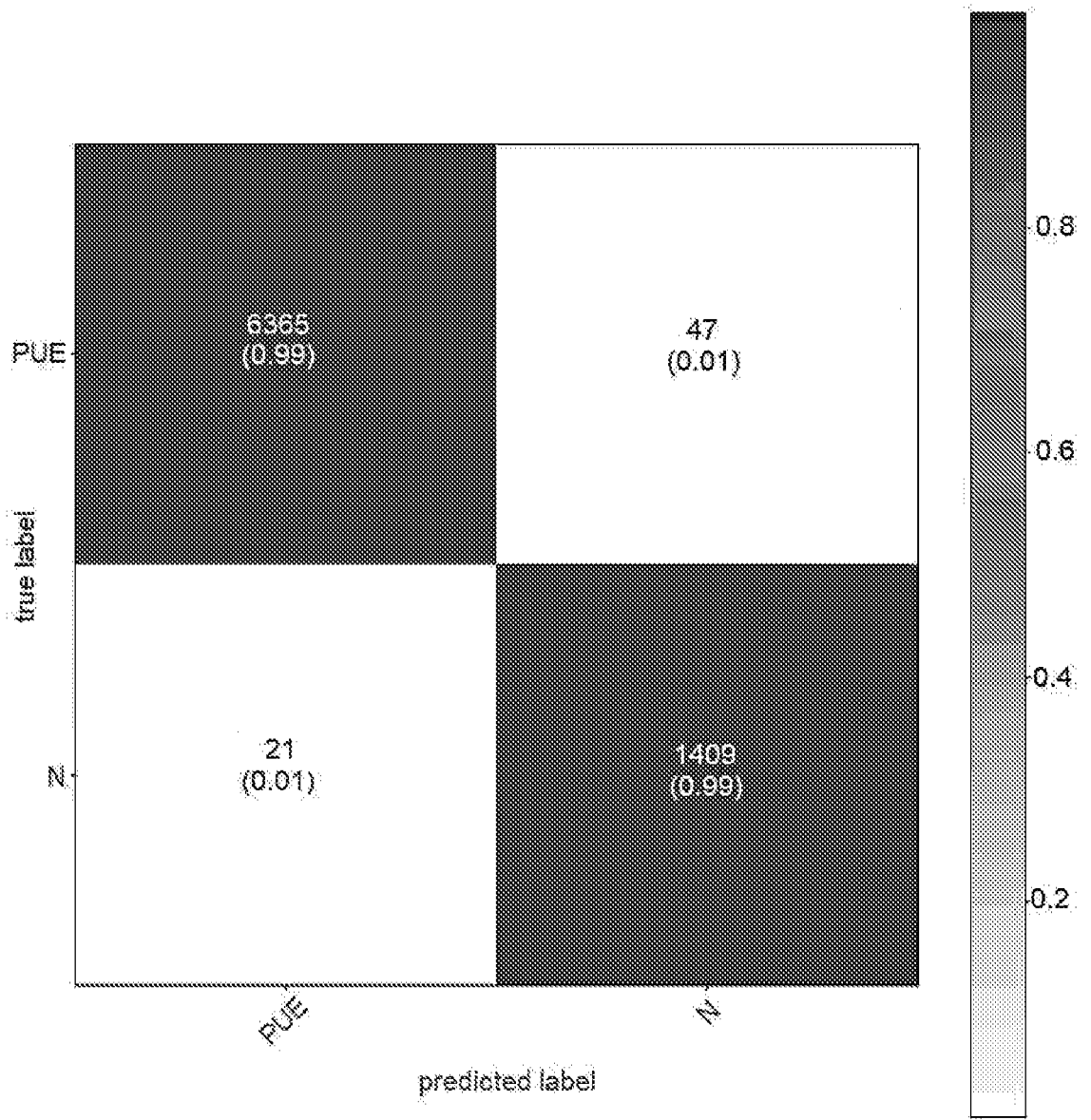
FIG. 9 illustrates an exemplary confusion matrix after training on a small subset of images and labelled data according to an embodiment of the present invention. Results used for model selection. Number of images of the small subset of data and respective class proportion between parentheses.

FIG. 9 illustrates an exemplary confusion matrix after training on a small subset of images and labelled data. Results used for model selection. Number of images of the small subset of data and respective class proportion between parentheses.

Figure 10:
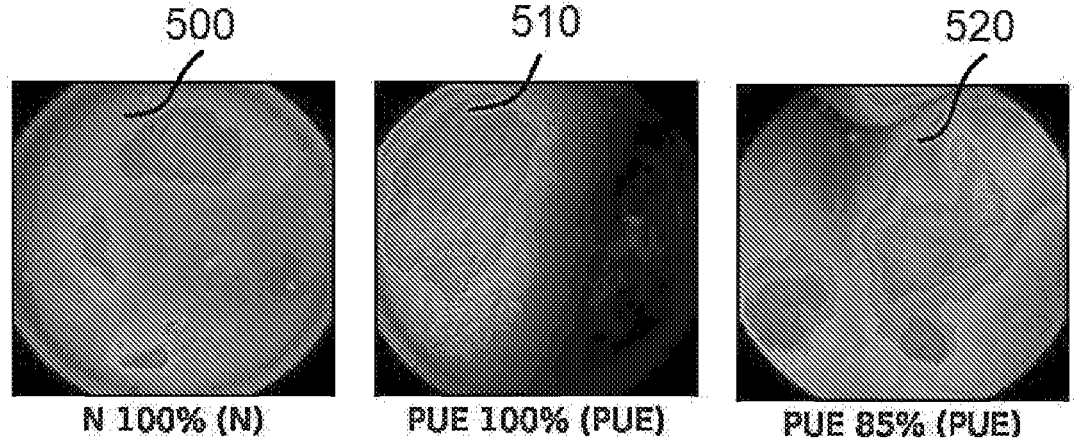
FIG. 10 illustrates examples of lesion classification according to an embodiment of the present invention.

FIG. 10 shows examples of lesion classification according to an embodiment of the present invention, where in 500 there is no lesion; in 510 there is a ulcer or erosion and in 520 there is a ulcer or erosion.

FIG. 11 shows a result of performing deep learning-based lesion classification on the data volume 240 and 250, according to an embodiment of the present invention. The results of small bowel and colon classification using the training method 8000 of the present invention are significantly improved as compared to the results using the existing methods (without method 8000).

Figure 12:
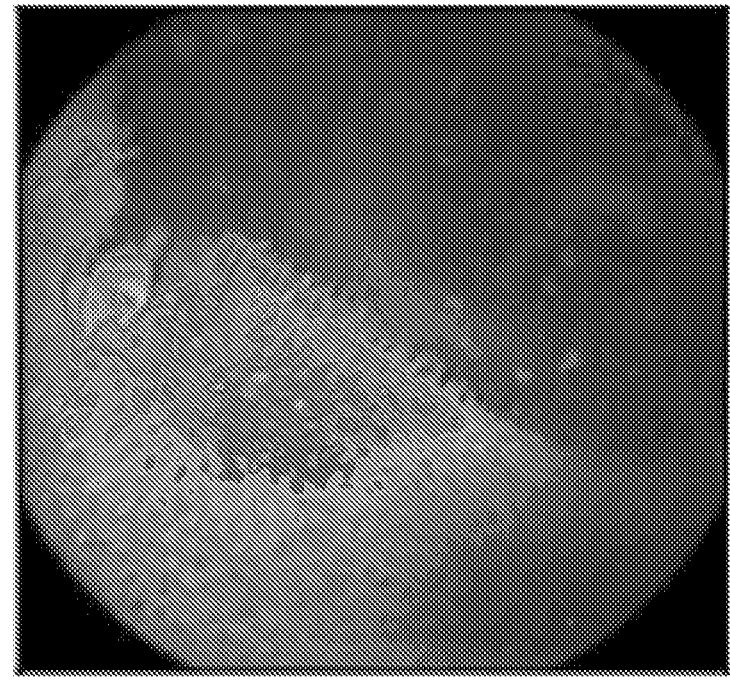
FIG. 12 illustrates an example of a classified lesion waiting for expert confirmation.

FIG. 12 shows an example of a classified lesion waiting for validation by the output collector module 7000. By another neural network or any other computational system adapted to perform the validation task, physician expert in gastroenterological imagery identifies small bowel and colon lesions, analyzing the labelled image classified by the deep model 140. Options for image reclassification on the last layer of the classification network 100 are depicted in FIG. 5. Optionally, confirmation or reclassification are sent to the storage module.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art within the scope of the appended claims.

The invention claimed is:

1. A computer-implemented method capable of automatically identifying erosions and ulcers in colon capsule colonoscopy medical images by classifying the pixels as erosions or ulcers comprising:

selecting a number of subsets of all colon capsule colonoscopy images, each of said subsets comprising only images from the same patient;

selecting another subset as validation set, wherein the another subset does not overlap chosen images in previously selected subsets;

pre-training of each chosen subset with one of a plurality of combinations of convolutional neural network image feature extraction component, followed by a subsequent classification neural network component for pixel classification as erosions and ulcers, wherein said pre-training;

stops early when the scores do not improve over a given number of epochs, namely three;

evaluates the performance of each of the combinations;

is repeated on new, different subsets, with another networks combination and training hyperparameters, wherein such new combination considers a higher number of dense layers if a f1-metric is low and fewer dense layers if the f1-metric suggests overfitting;

selecting the architecture combination that performs best during pre-training;

fully training and validating during training the selected architecture combination using the entire set of colon capsule colonoscopy images to obtain an optimized architecture combination;

prediction of erosions and ulcers using said optimized architecture combination for classification;

receiving the classification output of the prediction by an output collect module with means of communication to a third-party capable of performing validation by interpreting the accuracy of the classification output and of correcting a wrong prediction, wherein the third-party comprises at least one of: another neural network, any other computational system adapted to perform the validation task or, optionally, a physician expert in gastroenterological imagery; and storing the corrected prediction into the storage component.

2. The method of claim 1, wherein classification network architecture comprises at least two blocks, each having a Dense layer followed by a Dropout layer.

3. The method of claim 1, wherein a last block of the classification component includes a BatchNormalization layer followed by a Dense layer where a depth size is equal to a number of lesions of a type one desires to classify.

4. The method of claim 1, wherein a set of pre-trained neural networks is best performing among the following: VGG16, Inception V3, Xception, EfficientNetB5, EfficientNetB7, Resnet50 and Resnet125.

5. The method of claim 1, wherein a best performing combination is chosen based on overall accuracy and on f1-metrics.

6. The method of claim 1, wherein training of a best performing combination comprises two to four dense layers in sequence, starting with 4096 and decreasing in half up to 512.

7. The method of claim 1, wherein, between a final two layers of a best performing combination there is a dropout layer of 0.1 drop rate.

8. The method of claim 1, wherein training of the samples includes a ratio of training to-validation of 10%-90%.

9. The method of claim 1, wherein third-party validation is done by user-input.

10. The method of claim 1, wherein a training dataset includes images in a storage component that were predicted sequentially performing the method of claim 1.

11. A portable endoscopic device comprising instructions which, when executed by a processor, cause the computer to carry out the steps of the method of claim 1.

* * * * *